(12) United States Patent
Thomson et al.

(10) Patent No.: US 12,097,366 B2
(45) Date of Patent: Sep. 24, 2024

(54) SYSTEMS AND METHODS FOR MONITORING NEURAL ACTIVITY

(71) Applicant: MONASH UNIVERSITY, Clayton (AU)

(72) Inventors: Richard H. Thomson, Clayton (AU); Paul B. Fitzgerald, Clayton (AU); Caley Sullivan, Clayton (AU); Mark Harrison, Clayton (AU)

(73) Assignee: MONASH UNIVERSITY, Clayton (AU)

( * ) Notice: Subject to any disclaimer, the term of this patent is extended or adjusted under 35 U.S.C. 154(b) by 549 days.

(21) Appl. No.: 17/288,125

(22) PCT Filed: Oct. 25, 2019

(86) PCT No.: PCT/AU2019/051175
§ 371 (c)(1),
(2) Date: Apr. 23, 2021

(87) PCT Pub. No.: WO2020/082135
PCT Pub. Date: Apr. 30, 2020

(65) Prior Publication Data
US 2022/0118247 A1    Apr. 21, 2022

(30) Foreign Application Priority Data
Oct. 26, 2018 (AU) .................. 2018904064

(51) Int. Cl.
*A61N 1/08* (2006.01)
*A61N 1/05* (2006.01)
*A61N 1/20* (2006.01)

(52) U.S. Cl.
CPC ............. *A61N 1/08* (2013.01); *A61N 1/0534* (2013.01); *A61N 1/20* (2013.01)

(58) Field of Classification Search
CPC .......... A61N 1/08; A61N 1/0534; A61N 1/20
See application file for complete search history.

(56) References Cited

U.S. PATENT DOCUMENTS

| 4,595,010 A | 6/1986 | Radke |
| 8,190,248 B2 | 5/2012 | Besio |

(Continued)

FOREIGN PATENT DOCUMENTS

| CN | 106659894 A | 5/2017 |
| CN | 107666855 A | 2/2018 |

OTHER PUBLICATIONS

International Search Report and Written Opinion in corresponding Application No. PCT/AU2019/051175, dated Jan. 31, 2020 (11 pages).

(Continued)

*Primary Examiner* — Joseph M Dietrich
(74) *Attorney, Agent, or Firm* — Bookoff McAndrews, PLLC

(57) ABSTRACT

An apparatus for performing bioelectric stimulation, the apparatus comprising: a stimulation unit; a measurement unit comprising an amplifier; first and second stimulation electrodes operable to apply electrical signals to tissue of a patient; first and second measurement electrodes operable to receive first and second measurement signals from the tissue of the patient; wherein the stimulation unit is configured to deliver a first stimulation signal to the first stimulation electrode and a second stimulation signal to the second stimulation electrode; wherein the first signal and the second signal are mirrored about a biasing voltage, the biasing voltage set in dependence of the dynamic range of the amplifier.

20 Claims, 7 Drawing Sheets

(56) References Cited

U.S. PATENT DOCUMENTS

| | | |
|---|---|---|
| 8,660,650 B2 | 2/2014 | Nakashima et al. |
| 2002/0077670 A1 | 6/2002 | Archer et al. |
| 2012/0296390 A1 | 11/2012 | Nakashima et al. |
| 2016/0287112 A1 | 10/2016 | Mcfarlin et al. |
| 2017/0071490 A1 | 3/2017 | Parker et al. |
| 2018/0115320 A1 | 4/2018 | Sharma et al. |
| 2019/0357788 A1 | 11/2019 | Single |

OTHER PUBLICATIONS

Park et al., "A Novel Array-type Transcranial Direct Current Stimulation (tDCS) System for Accurate Focusing on Targeted Brain Regions," Digests of the 2010 14th Biennial IEEE Conference on Electromagnetic Field Computation, May 12, 2010, pp. 1-1, doi: 10.1109/2010.5481279 (1 page).

Valente et al., "Design of a Current-Steering Implantable Stimulator with Electric Field Shifting for Deep Brain Stimulation," 2010 Biomedical Circuits and Systems Conference (BioCAS), Nov. 5, 2010, pp. 162-165, doi: 10.1109/BIOCAS.2010.5709596.

SYSTEMS AND METHODS FOR MONITORING NEURAL ACTIVITY

TECHNICAL FIELD

The present disclosure relates to methods for monitoring neural activity during transcranial electrical stimulation (tES).

BACKGROUND

Transcranial electrical stimulation (tES) is a neural stimulation method whereby electric currents in the range 10 uA to 5 mA are typically passed through parts of a patient's brain via two or more stimulus electrodes. Usually temporary surface electrodes are used, however fully implanted electrodes may also be used. The current may be continuous "direct current" (DC) or time varying "alternating current" (AC).

Transcranial electrical stimulation (tES) is a form of non-invasive neural stimulation. It involves the delivery of low current electrical signals, typically in the range of 10 μA to 5 mA, to targeted regions of the brain using a pair of surface electrodes (anode and cathode) placed on the scalp of a patient or implanted into the brain. The application of tES has been shown to influence many aspects of mental activity, including perception, memory, cognition and emotion. Although the exact mechanism of action remains uncertain, its effects are mainly attributed to interactions with the electrochemical processing of neurons in the brain.

tES delivers a low current electrical signal that oscillates at a specified frequency of interest. It is thought that these externally applied oscillations can entrain and/or influence the endogenous oscillations of the brain, i.e. phase alignment of the brain oscillations to the externally applied oscillating electric currents, and modulation of spike-timing dependent plasticity.

Studies to date have been largely limited to investigating the neurophysiological after-effects of tES, or its influence on behaviour. There is, however, very little known about its effects on neural activity during stimulation, since conventional tES introduces large electrical artefacts and the magnitude of these artefacts relative to the underlying biological activity of interest make the underlying biological activity difficult to measure.

Attempts have been made to separate tES stimulation artefacts from underlying brain activity using principal component analysis, temporal filtering, and beamforming in MEG. These techniques have been found to be somewhat ineffective; a significant nonlinear artefact remains even when using such techniques. Additionally, these techniques may be unable to recover the underlying brain activity when the tES stimulation artefacts saturate or overload the amplifier used to monitor brain activity.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

According to an aspect of the disclosure, there is provided an apparatus for performing bioelectric stimulation, the apparatus comprising: a stimulation unit; a measurement unit comprising an amplifier; first and second stimulation electrodes operable to apply electrical signals to tissue of a patient; first and second measurement electrodes operable to receive first and second measurement signals from the tissue of the patient; wherein the stimulation unit is configured to deliver a first stimulation signal to the first stimulation electrode and a second stimulation signal to the second stimulation electrode; wherein the first signal and the second signal are substantially mirrored about a biasing voltage, the biasing voltage set in dependence of the dynamic range of the amplifier.

The measurement unit may be configured to generate a signal in dependence of a voltage difference between the first measurement signal the second measurement signal. The measurement unit may be configured to generate the signal in dependence of an average of the first measurement signal and the second measurement signal.

The first stimulation signal and the second stimulation signal may be oscillating signals or pulsed signals. The oscillating signals may be sinusoidal, sawtooth, squarewave, or arbitrary.

The first stimulation signal and the second stimulation signal may be direct current (DC) signals.

The biasing voltage may be set in dependence on the centre point of the dynamic range of the amplifier.

The stimulation unit and the measurement unit may share a common reference voltage. In which case, the biasing voltage may be adjusted in dependence on a DC offset between the common reference voltage and a common mode voltage measured at the first and second measurement electrodes. Additionally, or alternatively, the biasing voltage may be adjusted to reduce the DC offset between the common reference voltage and the common mode voltage measured at the first and second measurement electrodes.

The signal may be an electroencephalographic (EEG) signal.

The measurement unit may comprise a differential amplifier comprising: a first input coupled to the first measurement electrode, a second input coupled to the second measurement electrode, and an output.

The stimulation unit may comprise a current source having an output; an inverting amplifier having a non-inverting input and an inverting output; and a summing circuit having a first summing input, a second summing input and a summing output.

The output of the current source may be coupled to the first stimulation electrode and the first summing input. The inverting output of the inverting amplifier may be coupled to the second stimulation electrode. The second summing input may be coupled to a reference offset voltage. The summing output may be coupled to inverting input of the inverting amplifier.

The measurement circuit may comprise a feedback output and the measurement circuit may configured to output, at the feedback output, a voltage proportional to an average of a voltage on the first measurement electrode and a voltage on the second measurement electrode.

The output of the current source may be coupled to the first stimulation electrode and the first summing input. The second summing input may be coupled to the feedback output. The inverting input may be coupled to the summing output.

The apparatus may further comprise a stimulation compensation filter coupled between the first output of the current source and the first summing input.

The apparatus may further comprise a measurement compensation filter coupled between the feedback output and the second summing input.

The tissue may be brain tissue.

The first and second measurement electrodes may be transcranial, transdermal or implanted in the brain. Additionally or alternatively, the first and second stimulation electrodes may be transcranial, transdermal or implanted in the brain.

According to another aspect of the disclosure, there is provided a method of performing bioelectric stimulation, comprising: generating a first signal; generating a second signal wherein the first stimulation signal and the second stimulation signal are mirrored about a biasing voltage, the biasing voltage set in dependence of the dynamic range of an amplifier; applying the first signal to a first stimulation electrode operable to couple electrical signals into tissue of a patient; applying the second signal to a second stimulation electrode operable to couple electrical signals into the tissue of the patient; receiving first and second measurement signals from the tissue of the patient at first and second measurement electrodes; and amplifying the received electrical signals using the amplifier.

The method may further comprise: generating a signal in dependence of a voltage difference between the first measurement signal and the second measurement signal.

The measurement unit may be configured to generate the signal in dependence of an average of the first measurement signal and the second measurement signal.

The first stimulation signal and the second stimulation signal may be an oscillating signal or a pulsed signal. The oscillating signals may be sinusoidal, sawtooth, square-wave or arbitrary signals.

The first stimulation signal and the second stimulation signal may be direct current (DC) signals.

The biasing voltage may be set in dependence on the centre point of the dynamic range of the amplifier.

The second stimulation signal and the signal may be generated based on a common reference voltage.

The method may further comprise adjusting the biasing voltage in dependence on a DC offset between the common reference voltage and a common mode voltage of the first measurement signal and the second measurement signal.

The biasing voltage may be adjusted to reduce the DC offset between the common reference voltage and the common mode voltage.

The signal may be an electroencephalographic (EEG) signal.

The tissue may be brain tissue.

The first oscillating signal and/or the second oscillating signal may be applied transcranially, transdermally, or via an implanted electrode.

The first and second measurement electrodes may be transcranial, transdermal or implanted in the brain.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Figure 1:
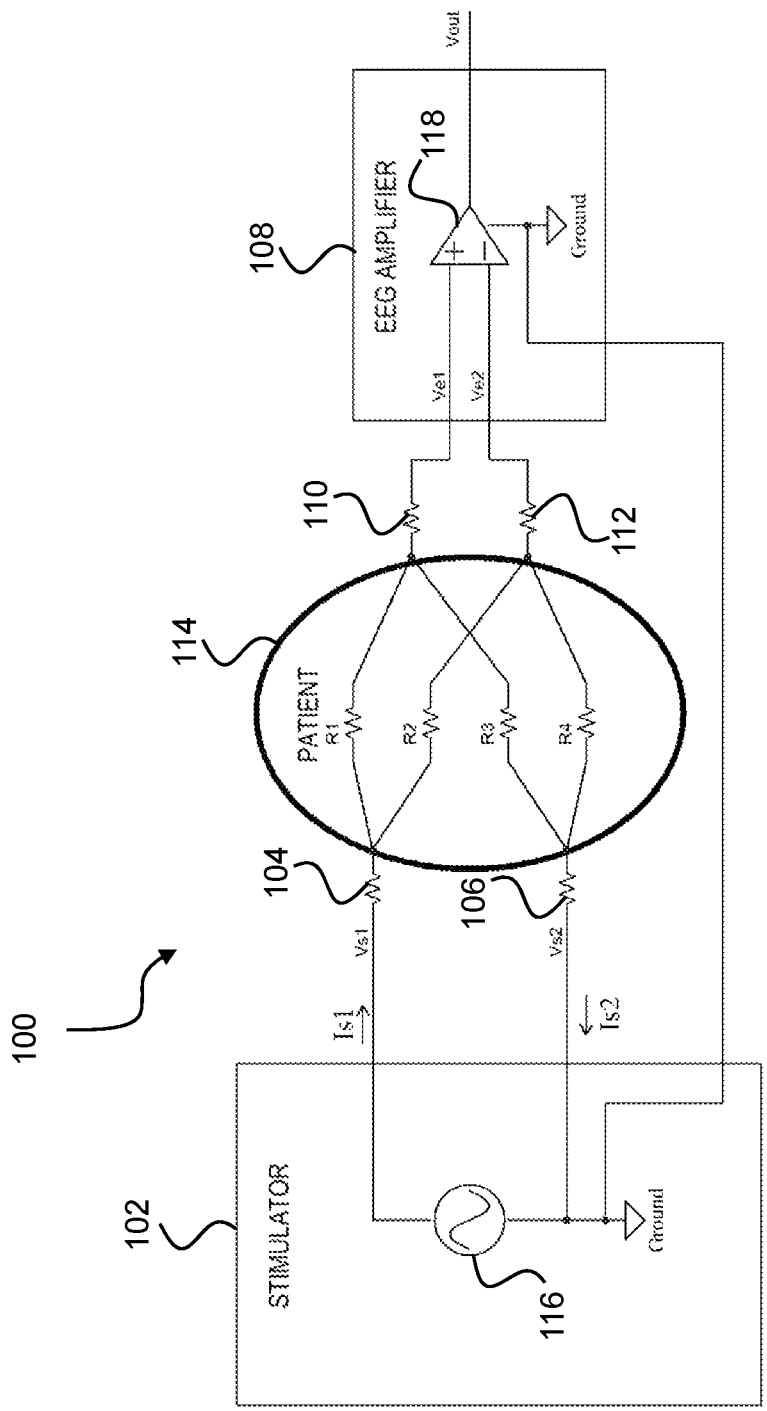
FIG. 1 is a circuit diagram of a known apparatus for electrical stimulation and measurement of biological tissue.

A known apparatus 100 for simultaneous tES stimulation and measurement is shown in FIG. 1. The apparatus comprises a stimulation unit 102 coupled to a pair of stimulation electrodes 104, 106 and an electroencephalograph (EEG) unit 108 coupled to a pair of measurement electrodes 110, 112. Each pair of electrodes 104, 106, 110, 112 may be fixed into contact with the scalp of a patient so that an electrical current can be delivered and measured using the stimulation electrodes 104, 106 and measurement electrodes 110, 112, respectively. Separate pairs of stimulation and measurement electrodes 104, 106, 110, 112 provide a degree of isolation between the higher voltages required to stimulation and the smaller EEG voltages to be measured. The patients head 114 is represented in FIG. 1 by an electrical head model known in the art and comprising a resistor network R1 to R4.

The stimulation unit comprises a current source 116 operable to deliver a controlled electrical current through neural tissues via the stimulation electrodes 104, 106. The electrical current delivered by the current source 116 is controlled to be independent of changes in tissue and electrode impedance(s). An alternating current is delivered to the first stimulation electrode 104 of the pair, and the second stimulation electrode 106 is maintained at a reference voltage, e.g., ground (0V).

The EEG unit 108 comprises an amplifier 118 configured to amplify fluctuations in voltage between the measurement electrodes 110, 112. Because voltage fluctuations associated with endogenous neural activity are very small, the EEG unit 108 is configured to be highly sensitive to voltage fluctuations across the measurement electrodes 110, 112. The sensitivity poses a problem since the impedance(s) of the electrodes 104, 106, 110, 112 can vary over time due to changes in applied pressure, tissue resistance and the fidelity of electrode contact with the scalp. An imbalance in the impedances of the stimulation electrodes 104, 106 lead to a change in stimulation voltage applied to the patient. Such a change in average tissue voltage in turn leads to a change in the common mode voltage measured at the measurement electrodes 110, 112. Changes in the common mode voltage can lead the EEG unit 108 to operate in a saturation mode or non-linear mode which, in turn, leads to inaccurate measurements of electrical activity in the brain 114.

Figure 2:
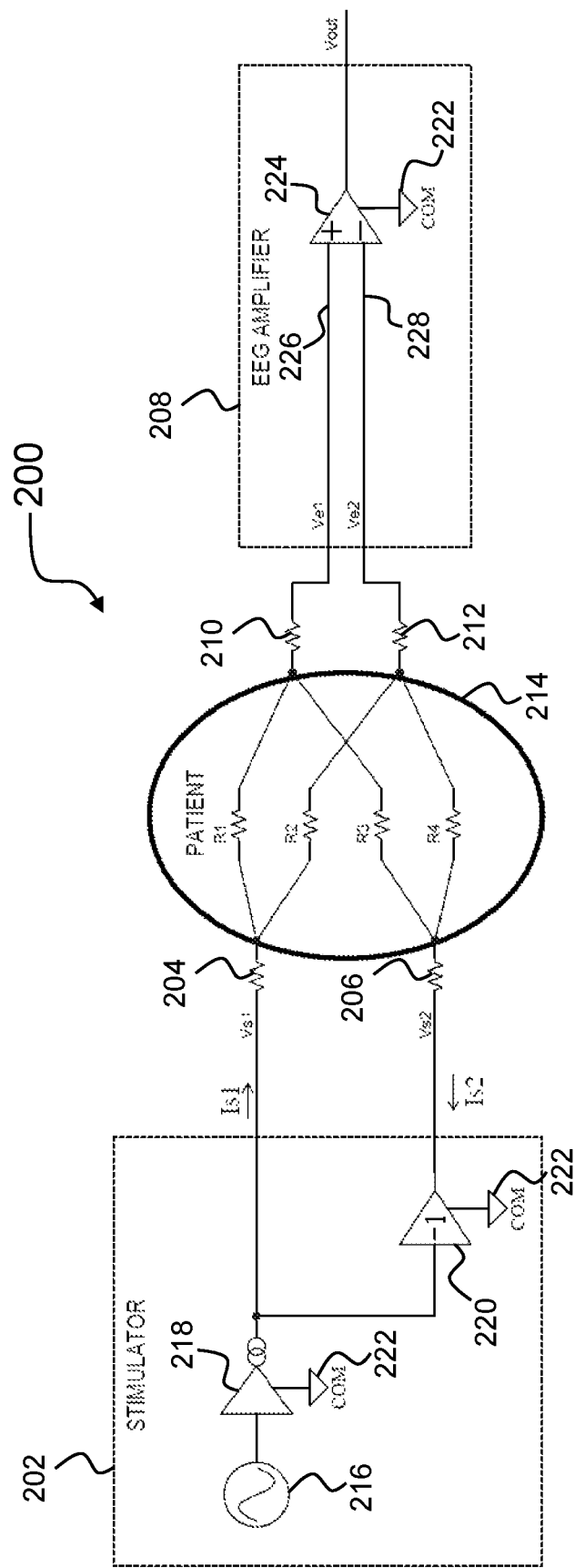
FIG. 2 is a circuit diagram of an apparatus for electrical stimulation and measurement of biological tissue according to an embodiment of the present disclosure.

Embodiments of the present disclosure overcome such problems by implementing a novel stimulation and measurement technique using a voltage mirroring differential current source. FIG. 2 is a schematic diagram of an apparatus 200 incorporating an exemplary voltage mirroring differential current source.

The apparatus 200 comprises a differential stimulation unit 202 coupled to first and second stimulation electrodes 204, 206 and an electroencephalograph (EEG) unit 208 coupled to first and second measurement electrodes 210, 212. As with the apparatus 100 show in FIG. 1, each electrode 204, 206, 210, 212 may be fixed into contact with the scalp of a patient so that an electrical current can be delivered and measured using the stimulation electrodes 204, 206 and measurement electrodes 210, 212, respectively. As with the apparatus 100 shown in FIG. 1, impedance(s) of the electrodes 204, 206, 210, 212 can vary dramatically over time. The patient's head 214 is again represented by a known electrical head model comprising a resistor network R1 to R4 representative of a neural structure in the brain.

The stimulation unit 202 comprises a signal generator 216, a voltage controlled current source 218 and an inverting voltage amplifier 220. An output of the signal generator 216 is coupled to an input of the voltage controlled current source 218 An output of the voltage controlled current source 218 is coupled to both an inverting input of the inverting amplifier 220 and the first stimulation electrode 204. An output of the inverting amplifier 220 is coupled to the second stimulation electrode 206. The voltage controlled current source 218 and the inverting amplifier 220 share a common reference voltage 222.

The EEG unit 208 comprises a differential amplifier 224. The first and second measurement electrodes 210, 212 are coupled to inverting and non-inverting inputs 226, 228 of the differential amplifier 224, respectively. The differential amplifier 224 shares the same common reference voltage 222 as the voltage controlled current source 218 and the inverting amplifier 220. The output voltage $V_{out}$ of the differential amplifier 224 is proportional to the difference between the voltages Ve1, Ve2 at the first and second measurement electrodes 210, 212 in accordance with the equation below.

$$V_{out} = \text{Gain} \times (Ve1 - Ve2)$$

Where Gain is the differential gain of the differential amplifier 224.

The stimulation unit 202 provides a voltage to the first and second stimulation electrodes 204, 206 which is of equal magnitude and opposite polarity. In other words, the stimulation unit 208 is configured to raise the potentials Vs1, Vs2 at the first and second stimulation electrodes 204, 206 to equal but opposite voltages with respect to the common reference voltage 222. Provided the patient's head 214 is isolated from the common reference voltage 222, and the input of the EEG unit 208 has a relatively high impedance compared to the impedances of the stimulation electrodes 204, 206 and the impedances of the patient's head R3, R4, then the current IS1 delivered to the first stimulation electrode 204 will be equal to the current IS2 delivered to the second stimulation electrode 206. The relatively high input impedance of the EEG unit 208 minimises current flow from the stimulation electrodes 204, 206 to the stimulation unit 202 via the measurement electrodes 210, 212 which in turn reduces unintended stray stimulation paths within the patient's head 214. This in turn can minimise electrical stimulation sensations around the contact area of the measurement electrodes 210, 212 which can be produced due by stray stimulation current.

By applying an opposite but equal voltage to the first and second stimulation electrodes 204, 206, the voltage difference presented to the patient's head 214 is approximately double that of the voltage presented using a conventional single ended bipolar current source, such as that shown in FIG. 1. Doubling the presented voltage has several benefits. Firstly, the same current may be delivered to twice the load impendence. Secondly, twice the current may be delivered to a given load impedance. In addition, the common mode stimulation voltage at the measurement electrodes 210, 212 is also reduced. This means that circuit components, including the current source 218, inverting amplifier 220 and the differential amplifier 224, may operate at lower voltages with respect to the common reference voltage 222.

The apparatus 200 of FIG. 2 also substantially reduces stray currents flowing from the stimulation unit 202 to the EEG unit 208 via the patient's head 214 by reducing voltage coupled through stray capacitive and resistive couplings that exist between the head 214 and the common reference voltage 222.

Whilst the apparatus 200 shown in FIG. 2 provides several advantages over conventional tES stimulators, some of the same drawbacks as those associated with the apparatus 100 shown in FIG. 1 remain with the apparatus 200 shown in FIG. 2.

Under ideal conditions, impedances of the stimulation electrodes 204, 206 would preferably be equal, causing the voltage drop across the first and second stimulation electrodes 204, 206 to be equal in magnitude. Additionally, under ideal conditions, the tissue impedances R1 to R4 of the patient's head 214 would also be equal, such that the voltages of the first and second measurement electrodes 210, 212 would be zero with respect to the common reference voltage 222, due to the equal magnitude by opposite polarities of Vs1 and Vs2.

In practice, however, the impedances of the first and second stimulation electrodes 204, 206 are likely to differ, causing the potential of the head 214 to be offset relative to the common reference voltage 222. The voltages at the first and second measurement electrodes 210, 212 may also be offset, causing the differential amplifier 224 to operate outside of its common mode working range, particularly since the differential amplifier 224 shares a common reference voltage 222 with the stimulation unit 202.

It is also likely, in practice that the impedance ratios R1/R2 and R3/R4 in the patient's head will not be equal, leading to the generation of a minor differential artefact voltage across the first and second measurement electrodes 210, 212. This artefact would then be amplified by the EEG unit 208 along with the endogenous neural EEG signal, degrading the signal to noise performance of the apparatus 200. This artefact may be reduced or removed using signal processing techniques known in the art, such as filtering or adaptive cancellation. However, such techniques increase the complexity and costs associated with tES.

Figure 3:
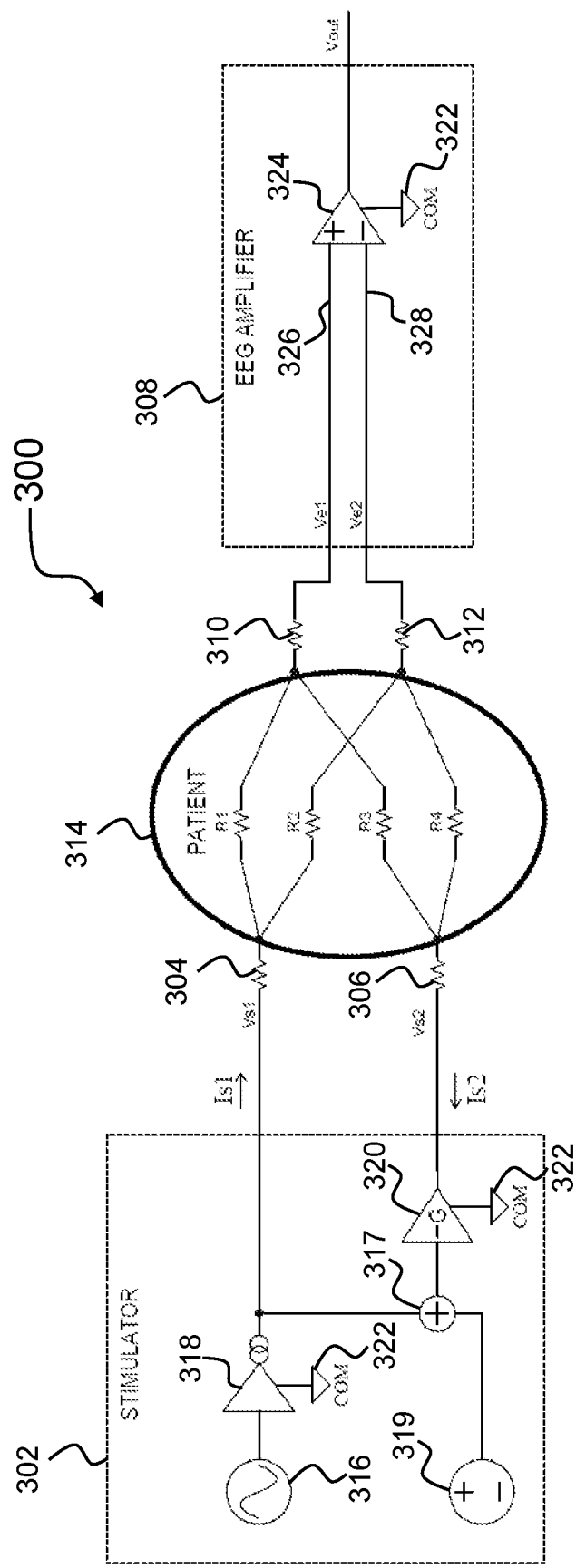
FIG. 3 is a circuit diagram of an apparatus for electrical stimulation and measurement of biological tissue according to an embodiment of the present disclosure.

To attend to some of the drawbacks associated with the apparatus 200 shown in FIG. 2, a further apparatus 300 for tES is proposed in FIG. 3.

The apparatus 300 comprises a differential stimulation unit 302 coupled to first and second stimulation electrodes 304, 306 and an electroencephalograph (EEG) unit 308 coupled to first and second measurement electrodes 310, 312. As with the apparatus 100, 200 shown in FIGS. 1 and 2, each electrode 304, 306, 310, 312 may be fixed into contact with the scalp of a patient so that an electrical current can be delivered and measured using the stimulation electrodes 304, 306 and measurement electrodes 310, 312, respectively. The patient's head 314 is again represented by known electrical head model comprising a resistor network R1 to R4 representative of a neural structure in the brain.

As with the stimulation unit 202 of FIG. 2, the stimulation unit 302 comprises a signal generator 316, a voltage controlled current source 318 and an inverting voltage amplifier 320. However, these elements of the stimulation unit 302 are configured slightly differently to those of the stimulation unit 202 shown in FIG. 2.

Specifically, an output of the signal generator is coupled to an input of the voltage controlled current source 318. An output of the voltage controlled current source 318 is coupled to the first stimulation electrode 304 as well as a first summing input of a summing circuit 317. A second summing input of the summing circuit 317 is coupled to an output of a fixed offset voltage generator 319 which itself is configured to generate and deliver an offset voltage $V_{offset}$ to the summing circuit 317. An output of the summing circuit 317 is coupled to an inverting input of the inverting amplifier 320. An output of the inverting amplifier 320 is coupled to the second stimulation electrode 306. The voltage controlled current source 318 and the inverting amplifier 320 share a common reference voltage 322.

In a variation of the arrangement shown in FIG. 3, the summing circuit 317 and inverting voltage amplifier 320 may be replaced by a differential amplifier with both inverting and non-inverting inputs. In such a variation, the output of the fixed offset voltage generator 319 is coupled to the non-inverting input of the differential amplifier and the output of the voltage controlled current source 318 is coupled to the inverting input of the differential amplifier.

The EEG unit 308 comprises a differential amplifier 324 configured in the same manner as the differential amplifier 224 of the apparatus 200 shown in FIG. 2 with first and second measurement electrodes 310, 312 coupled to inverting and non-inverting inputs 326, 328 of the differential amplifier 324, respectively. The differential amplifier 324 shares the same common reference voltage 322 as the voltage controlled current source 318 and the inverting amplifier 320.

As described above with reference to FIG. 2, imbalances in electrode and tissue impedances may cause the common mode voltage levels at the measurement electrodes 310, 312 to be sub-optimal and thus degrade the signal-to-noise ratio of the measured EEG signal. The stimulation unit 302 operates to minimize the common mode voltage artefact between the first and second measurement electrodes 310, 312 by adding an offset voltage to the voltage Vs2 applied to the second stimulation electrode 306. The common mode voltage at the measurement electrodes 310, 312 may be reduced by controlling the offset voltage and the gain of the inverting amplifier 320. By adjusting the offset voltage, the voltage applied to the second stimulation electrode 306 can be biased relative to the common reference 322. By adjusting the gain of the inverting amplifier 322, the amplitude of the voltage applied to the second stimulation electrode 306 can be adjusted. Due to the inherent nature of the voltage controlled current source 318, the voltage difference between the first and second stimulation electrodes 304, 306 is proportional only to the stimulation current Isl and the impedance between the first and second simulation electrodes 304, 306. Changing the voltage of the second stimulation electrode 306 will cause the current source 318 to adjust the voltage at the first stimulation electrode 304 by the same amount so that the current Isl at the first stimulation electrode 304 is maintained. In turn the common mode voltage at the measurement electrodes 310, 312 will also track the conditions at the second stimulation electrode 306.

The offset voltage may be adjusted manually. Preferably, however, the offset voltage is programmed and/or controlled based on the common mode voltage at the first and second measurement electrodes 310, 312, so as to maintain optimum conditions for measurement at the EEG unit 308. The offset voltage may be controlled automatically using, for example, analogue closed loop control or digital closed loop control.

It will be appreciated that although the apparatus 300 shown in FIG. 3 is an improvement over that shown in FIGS. 1 and 2, as with the apparatus 200 of FIG. 2, the common mode voltage seen at the EEG unit 308 is still dependent on the impedances of the first and second stimulation electrodes 304, 306 and the placement of the measurement electrodes 310, 312 with respect to the stimulation electrodes 304, 306. In order to accommodate for changes in electrode impedance, continuous adjustment of offset voltage at the offset voltage generator and gain of the inverting amplifier 320.

The apparatus 400 shown in FIG. 4 overcomes these obstacles as will be described in more detail below.

The apparatus 400 comprises a differential stimulation unit 402 coupled to first and second stimulation electrodes 404, 406 and an electroencephalograph (EEG) unit 408 coupled to first and second measurement electrodes 410, 412. As with the apparatus 100, 200, 300 shown in FIGS. 1 to 3, each electrode 404, 406, 410, 412 may be fixed into contact with the scalp of a patient so that an electrical current can be delivered and measured using the stimulation electrodes 404, 406 and measurement electrodes 410, 412, respectively. The patient's head 414 is again represented by known electrical head model comprising a resistor network R1 to R4 representative of a neural structure in the brain.

As with the stimulation units 202, 302 of FIGS. 2 and 3, the stimulation unit 402 comprises a signal generator 416, a voltage controlled current source 418 and an inverting voltage amplifier 420. However, these elements of the stimulation unit 402 are provided in a different configuration to those shown in FIGS. 2 and 3.

Specifically, an output of the signal generator 416 is coupled to an input of the voltage controlled current source 418. An output of the voltage controlled current source 418 is coupled to the first stimulation electrode 404. The output of the voltage controlled current source 418 is also coupled to a first summing input of a summing circuit 417, optionally via a stimulation compensation filter 415. The summing circuit 417 receives at a second input a common mode error feedback signal 421 from the EEG unit 408, explained in more detail below. An output of the summing circuit 417 is coupled to an inverting input of the inverting amplifier 420. An output of the inverting amplifier 420 is coupled to the second stimulation electrode 406. The voltage controlled current source 418 and the inverting amplifier 420 share a common reference voltage 422.

Figure 4:
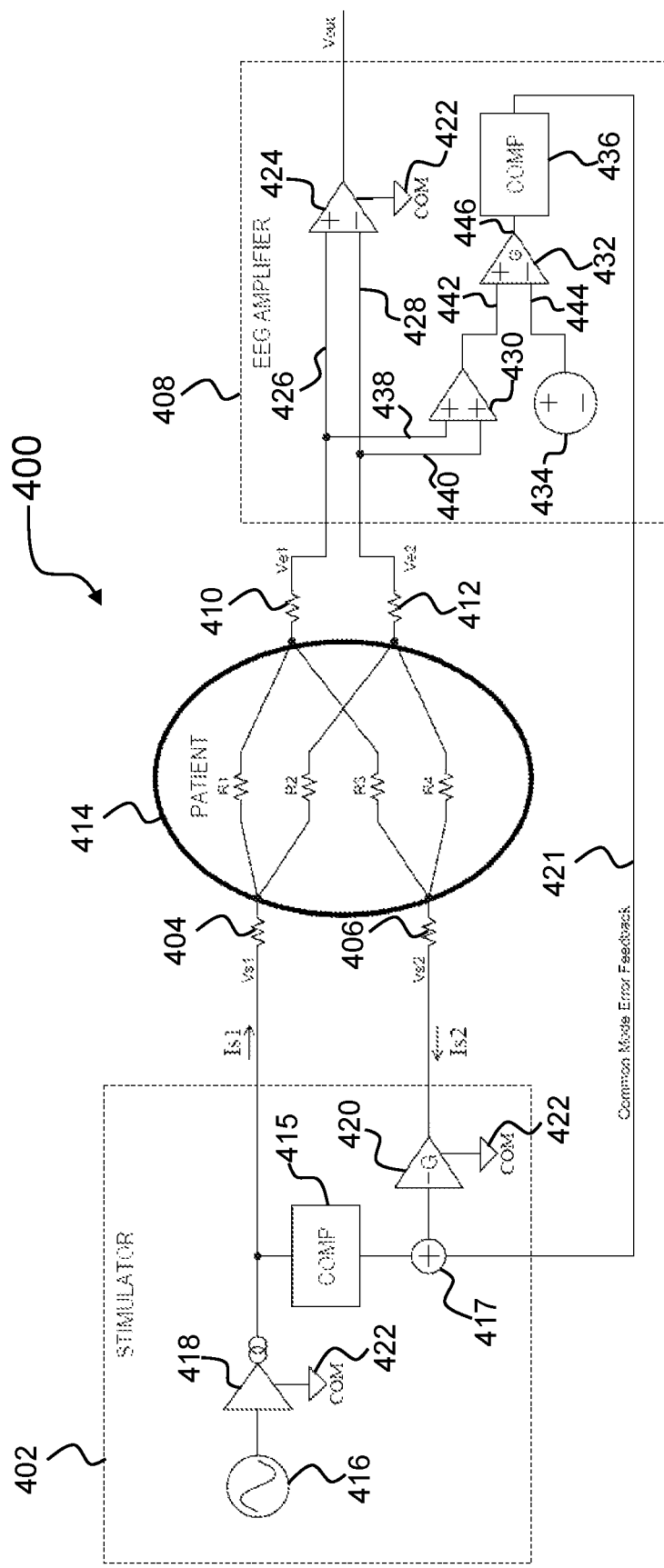
FIG. 4 is a circuit diagram of an apparatus for electrical stimulation and measurement of biological tissue according to an embodiment of the present disclosure.

In a variation of the arrangement shown in FIG. 4, the summing circuit 417 and inverting voltage amplifier 420 may be replaced by a differential amplifier with both inverting and non-inverting inputs. In such a variation, the common mode feedback signal 421 is fed to the inverting input of the differential amplifier and the output of the voltage controlled current source 418 is coupled to the inverting input of the differential amplifier (optionally via the compensation filter 415).

The EEG unit 408 comprises a first differential amplifier 424 with the first and second measurement electrodes 410, 412 coupled to inverting and non-inverting inputs 426, 428 of the first differential amplifier 424, respectively. The first differential amplifier 424 shares the same common reference voltage 422 as the voltage controlled current source 418 and the inverting amplifier 420.

The EEG unit 408 further comprises an averaging circuit 430, a second differential amplifier 432, an offset voltage generator 434 and a measurement compensation filter 436.

The first and second measurement electrodes 410, 412 are coupled to first and second inputs 438, 440 of the averaging circuit 430. An output of the averaging circuit 430 is coupled to a non-inverting input 442 of the second differential amplifier 432. The offset voltage generator 434 is configured to generate and provide an offset voltage $V_{offset}$ to an inverting input 444 of the second differential amplifier 432. An output of the second differential amplifier 432 is coupled to an input of the measurement compensation filter 436. An output of the measurement compensation filter 436 is configured to output the common mode error feedback signal 421 to the second summing input of the summing unit 417.

The apparatus 400 is configured to optimise the common mode voltage at the measurement electrodes 410, 412 by applying an error voltage $V_{error}$ to the second stimulation electrode 406. The averaging circuit 430 is configured to output an average of the voltages at the first and second measurement electrodes 410, 412 which represents the common mode voltage at the first and second measurement electrodes 410, 412. The determined common mode voltage is provided to the second differential amplifier 432 which outputs a common mode error signal 446 equal to the difference between the determined common mode voltage and the offset voltage $V_{offset}$ output by the offset voltage generator 434. The common mode error signal 446 represents an error between the actual common mode voltage the optimum common mode voltage for maximising performance of the first differential amplifier 424. The second differential amplifier 432 may also apply gain, G, to the common mode error signal 446. The common mode error signal 446 is filtered by the measurement compensation filter 436, to provide a filtered version 421 of the common mode error signal 446. The filtered common mode error signal 421 is coupled via the summing circuit 417 and inverting amplifier 420 to the second stimulation electrode 406, thus completing the negative feedback loop and minimizing the actual common mode voltage at the first and second measurement electrodes 410, 412.

The measurement compensation filter 436 is provided to increase the stability of the feedback loop. The phase and frequency characteristics of the measurement compensation filter 436 are chosen so as to achieve stability under a wide range of operating conditions.

Provided the stimulation waveform applied to the first stimulation electrode 404 is composed of frequency components that fall substantially within the bandwidth of the feedback loop, then the feedback-corrected voltage applied to the second stimulation electrode 406 should substantially cancel the influence of the voltage at the first stimulation electrode 404 on the common mode voltage at the first and second measurement electrodes 410, 412. However, problems may arise if the stimulation waveform applied to the first stimulation electrode 404 comprises frequency components that fall outside of the bandwidth of the feedback loop (for instance higher order harmonics). The stimulation compensation filter 415 may be configured to address such problems by providing a feed-forward signal to the second stimulation electrode 406 to minimise errors associated with frequency components of the stimulation waveform which fall outside the bandwidth of the feedback loop.

The compensation filter 415 may provide a path for high frequency voltage components of the stimulation waveform applied the first stimulation electrode 404 to generate and apply an opposing voltage to the second stimulation electrode 406 that may in turn minimise high frequency components present in the common mode voltage at the measurement electrodes 410, 412.

It will be appreciated that the loop frequency and phase response of the feedback loop is a product of the frequency responses of complex impedances of the electrodes 404, 406, 410, 412, the amplifiers 430, 432, and the measurement compensation filter 436. Accordingly, in some embodiments, the resultant feed-forward compensation path may have complimentary frequency and phase responses to those of the feedback loop.

In some embodiments, the characteristics of the compensation filter 415 may be controlled adaptively.

By providing the compensation filter 415, the common mode voltage at the measurement electrodes 410, 412, any residual stimulus artefacts and any biological signals may be maintained within the linear input voltage range of the EEG amplifier 424.

Figure 5:
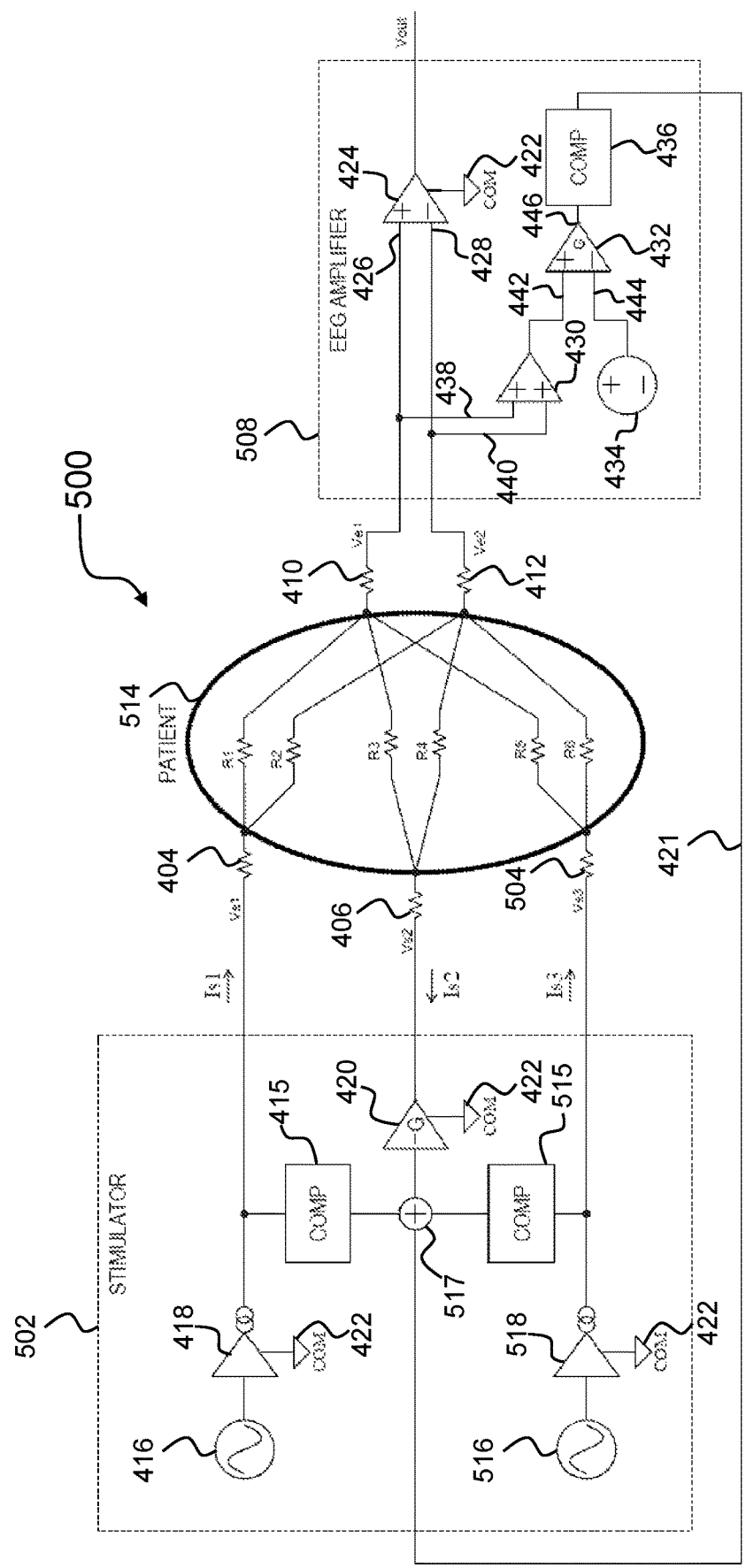
FIG. 5 is a circuit diagram of an apparatus for electrical stimulation and measurement of biological tissue according to an embodiment of the present disclosure.

The above described apparatus 400 may be adapted to drive more than two electrodes, for example using more than one current source. FIG. 5 shows an example apparatus 500 similar to the apparatus 400 shown in FIG. 4, adapted for use with two current sources configured to drive three stimulus electrodes. In FIG. 5, elements common to the apparatus 400 of FIG. 4 have been denoted with like numbering to the numbering used in FIG. 4.

In addition to the components of the stimulation unit 402 shown in FIG. 4, the stimulation unit 502 of the apparatus 500 shown in FIG. 5 further comprises a second signal generator 516, a second voltage controlled current source 518, a second stimulation compensation filter 515. In addition to the first and second electrodes 404, 406, a third stimulation electrode 504 is also provided. An EEG unit 508 is also provided, the elements and configuration of which are substantially identical to the EEG unit 408 shown in FIG. 4.

The apparatus 500 comprises a differential stimulation unit 502 and an EEG unit 508. The elements and configuration of the EEG unit 508 are substantially identical to the EEG unit 408 shown in FIG. 4.

The differential stimulation unit 502 is coupled to first second and third stimulation electrodes 404, 406, 504 and the electroencephalograph (EEG) unit 508 coupled to first and second measurement electrodes 410, 412.

As with the apparatus 400 shown in FIG. 4, each electrode 404, 406, 504, 410, 412 may be fixed into contact with the scalp of a patient so that an electrical current can be delivered and measured using the stimulation electrodes 404, 406, 504 and measurement electrodes 410, 412, respectively. The patient's head 514 is represented by known electrical head model comprising a resistor network R1 to R6 representative of a neural structure in the brain.

As with the stimulation units 402 of FIG. 4, the stimulation unit 502 comprises a signal generator 416, a voltage controlled current source 418, an inverting voltage amplifier 420, a stimulation compensation filter 415, and a summing circuit 517. In addition, the stimulation unit 502 further comprises a second signal generator 516, a second voltage controlled current source 518, a second stimulation compensation filter 515.

An output of the signal generator 416 is coupled to an input of the voltage controlled current source 418. An output of the voltage controlled current source 418 is coupled to the first stimulation electrode 404. The output of the voltage controlled current source 418 is also coupled to a first summing input of a summing circuit 417, optionally via a stimulation compensation filter 415.

An output of the second signal generator 516 is coupled to an input of the second voltage controlled current source 518. An output of the second voltage controlled current source 518 is coupled to the third stimulation electrode 504. The output of the first voltage controlled current source 418 is also coupled to a second summing input of the summing circuit 517, optionally via a second stimulation compensation filter 515. An output of the inverting amplifier 420 is coupled to the second stimulation electrode 406. The voltage controlled current source 418, the second voltage controlled current source 518, and the inverting amplifier 420 share a common reference voltage 422.

The summing circuit 417 receives at a third input a common mode error feedback signal 421 from the EEG unit 508, which is configured and operates in a similar manner to the EEG unit 408 of FIG. 4 to generate a (optionally filtered) common mode error feedback signal 421. An output of the summing circuit 417 is coupled to an inverting input of the inverting amplifier 420. An output of the inverting amplifier 420 is coupled to the second stimulation electrode 406.

During operation, the summing circuit 517 adds the voltages from the optional feed-forward signals output from the stimulation compensation filter 415 and the second stimulation compensation filter 515 to the common mode error feedback signal 421 received from the EEG unit 508. As such, the current Is2 in the second stimulation electrode 406 is driven to be equal to the sum of the current Is1 in the first stimulation electrode 404 and the current Is3 in the third stimulation electrode 504. The apparatus 500 acts in a similar manner to the apparatus 400 of FIG. 4, in that the common mode error feedback signal applied to the second stimulation electrode minimizes the actual common mode voltage at the first and second measurement electrodes 410, 412.

The stimulation compensation filter 415 and the second stimulation compensation filter 515 may be configured to provide a feed-forward signals to the second stimulation electrode 406 to minimise errors which fall outside the bandwidth of the negative feedback loop implemented using the common mode error feedback signal 421. To that end, each of the stimulation compensation filter 415 and the second stimulation compensation filter 515 may be configured in a similar manner to the stimulation compensation filter 415 described with reference to FIG. 4.

It will be appreciated that stimulation compensation filter 415 and the second stimulation compensation filter 515 are optional and may not be required if the stimulus waveforms applied to the first and third stimulation electrodes 404, 504 contain frequency components that fall within the frequency and phase responses of the feedback loop 421. Equally, in some embodiments, only one of the stimulation compensation filter 415 and the second stimulation compensation filter 515 may be required. For instance, if the waveform 516 has a high frequency component falling outside of the frequency and phase responses of the feedback loop 421 but the waveform 416 has a high frequency component falling within the frequency and phase responses of the feedback loop 421, then only the second stimulation compensation filter 515 may be required.

FIG. 5 illustrates the scalability of apparatus described herein. In FIG. 5, one additional signal generator is provided. In other embodiments, n additional signal generators may be used, where n is a positive integer. For example, multiple signal generators may be provided to generate complex electric field potentials within the stimulated tissue. This may be accomplished by modulating one or more of amplitude, frequency and phase of a plurality of independent stimulation signals in superposition.

Embodiments described herein allow for these complex fields to be controlled, since the shared common reference voltage 222, 322, 422 can account for stray currents and nonlinearities associated with coupling electrical apparatus with biological tissue.

Furthermore the capacity to simultaneous measure signals at the patient's head allows for feedback control and source localisation of the resulting electric field effects.

In FIGS. 4 and 5 described above, a single differential amplifier 424 is used to in combination with two measurement electrodes 410, 412 both to measure endogenous neural activity in the brain. Additionally, only two measurement electrodes 410, 412 are used for the measurement of common mode voltage. However, embodiments of the present disclosure are not limited to the use of a single pair of measurement electrodes.

Figure 6:
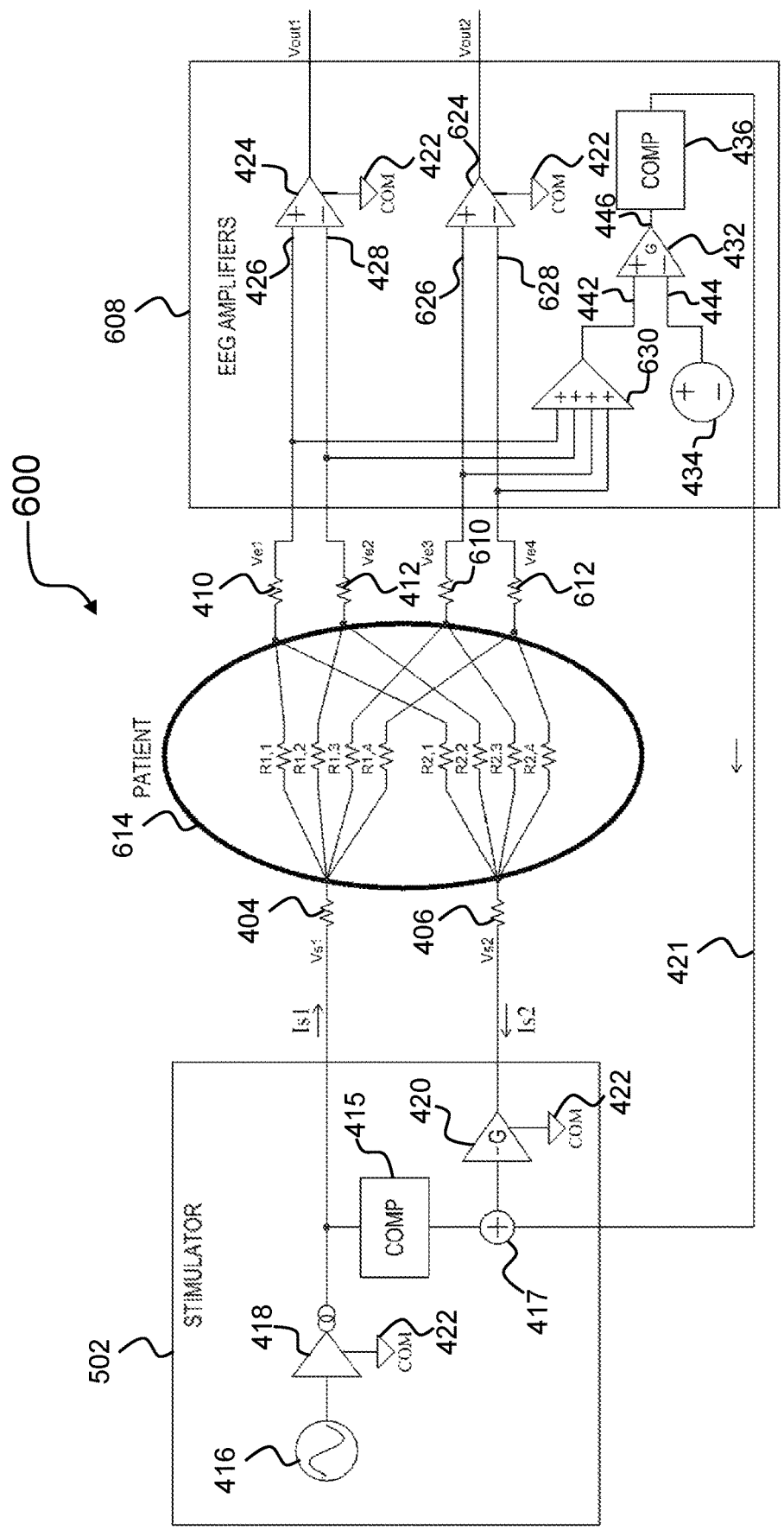
FIG. 6 is a circuit diagram of an apparatus for electrical stimulation and measurement of biological tissue according to an embodiment of the present disclosure.

In some embodiments, for example, multiple sets of electrodes (each comprising two or more electrodes) may be provided to measure EEG activity from one or more tissue regions. FIG. 6 shows an example apparatus 600 similar to apparatus 400 shown in FIG. 4, adapted to include two sets of measurement electrodes. In FIG. 6, elements common to the apparatus 400 of FIG. 4 have been denoted with like numbering to the numbering used in FIG. 4.

In addition to the components of the measurement unit 408 shown in FIG. 4, the EEG unit 608 of the apparatus 600 shown in FIG. 6 further comprises a third differential amplifier 624. In addition to the first and second measurement electrodes 410, 412, third and fourth measurement electrodes 610, 612 are also provided. The third and fourth measurement electrodes 610, 612 are coupled to respective non-inverting and inverting inputs 626, 628 of the third differential amplifier 624. The averaging circuit 430 of the apparatus 400 shown in FIG. 4 is replaced in FIG. 6 with a multi-input averaging circuit 630 and two or more of the first, second, third and fourth measurement electrodes 410, 412, 610, 612 are each coupled to an input of the multi-input averaging circuit 630. It will be appreciated that the multi-input average circuit 630 may use any two or more of the signals from the first, second, third and fourth measurement electrodes 410, 412, 610, 612. Optionally, inputs of the multi-input averaging circuit 630 may be equally weighted or weighted differently so as to weight signals received from two or more of the measurement electrodes 410, 412, 610, 612.

As with the apparatus 400 shown in FIG. 4, each electrode 404, 406, 410, 412, 610, 612 may be fixed into contact with the scalp of a patient so that an electrical current can be delivered and measured using the stimulation electrodes 404, 406 and measurement electrodes 410, 412, 610, 612 respectively. The patient's head 614 is represented by known electrical head model comprising a resistor network R1.1, R1.2, R1.3, R1.3, R2.1, R2.2, R2.3, R2.4 representative of a neural structure in the brain.

EEG measurements received at the multiple sets of electrodes 410, 412 610, 612 may be combined to generate a more accurate measurement of endogenous neural activity. Additionally or alternatively, measurements of common mode voltage received at multiple sets of electrodes may be combined to generate an average common mode voltage. An average common mode voltage error may be used in closed loop control to compensate for least average error.

In the embodiment shown in FIG. 6, a differential amplifier is provided for each set of electrodes to measure endogenous neural activity. In other embodiments, a single differential amplifier may be multiplexed between multiple sets of electrodes, such as the two pairs of measurement electrodes 410, 412, 610, 612 shown in FIG. 6.

In the embodiment shown in FIG. 6, a common mode voltage feedback error circuit is provided for all of the multiple sets of electrodes, multiplexed between all of the multiple sets of electrodes 410, 412, 610, 612. In other embodiments, a common mode voltage feedback error circuit such as that shown in FIGS. 4 and 5 (comprising the averaging circuit 430, offset voltage generator 434 and differential amplifier 432) may be provided for each set of electrodes to generate a common mode voltage feedback error signal for each set of electrodes.

FIGS. 5 and 6 described above illustrate variations of the apparatus of FIG. 4 with an increase in stimulation electrodes and measurement electrodes respectively. It will be appreciated that these variations are not mutually exclusive and embodiments of the present disclosure extend to apparatus having any number of stimulation electrodes, measurement electrodes and any associated stimulation or measurement circuitry described above in relation to each of FIGS. 4 to 6. For example, some embodiments may incorporate the stimulation unit 502 and stimulation electrodes 404, 406, 504 of FIG. 5 and the measurement unit 608 and measurement electrodes 410, 412, 610, 612 of FIG. 6.

Figure 7:
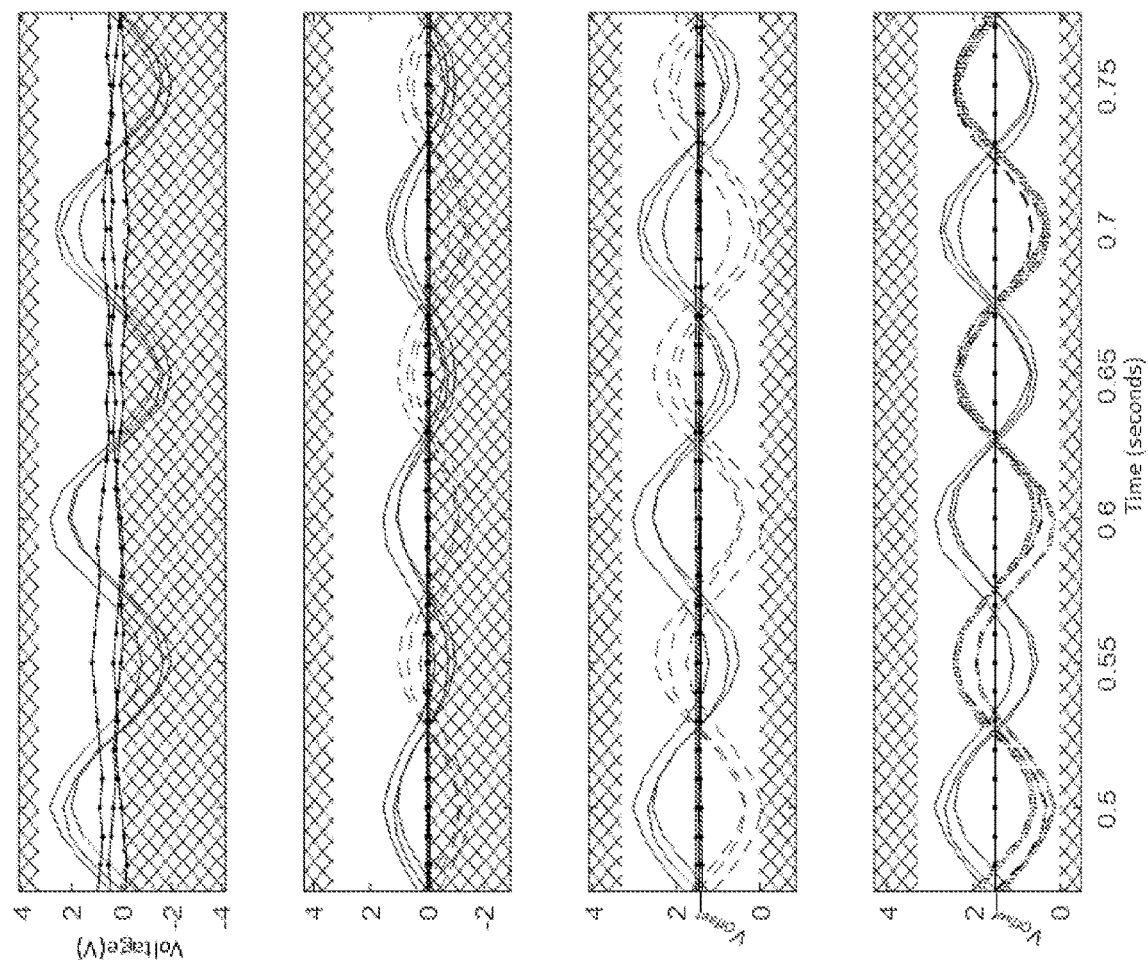
FIGS. 7A to 7D graphically illustrate the stabilizing effects of the apparatus shown in FIGS. 2 to 6.

FIGS. 7A to 7D graphically illustrate the stabilizing effects of the various stimulation and measurement techniques described above on body potentials. FIG. 7A corresponds to the prior art apparatus 100 shown in FIG. 1. FIG. 7B corresponds to the apparatus 200 shown in FIG. 2 incorporating a voltage mirroring differential current source. FIG. 7C corresponds to the apparatus 300 shown in FIG. 3 in which an offset bias is applied to the second stimulation electrode 306. FIG. 7D corresponds to the apparatus 400 shown in FIG. 4 which incorporates active feedback control of the common mode voltage at the measurement electrodes 410, 412. In each plot, the white area between the hatched areas illustrates the optimal dynamic range of the respective EEG amplifier used to measure endogenous neural activity. The hatched area fall outside of this range.

FIG. 7A shows a single biphasic signal applied using the apparatus 100 shown in FIG. 1, repeated three times with random noise added to each repetition. An alternating current is delivered to the first stimulation electrode 104 of the pair, and the second stimulation electrode 106 is maintained at a reference voltage, e.g., ground (0V). The signal (solid line) represents the voltage applied at the first stimulation electrode 104 output of a constant current source. Added random noise on each repetition simulates the unpredictable fluctuations in voltage needed to maintain a constant current. The dotted black line represents the body ground reference (Vref) as seen by the bulk of patient's head. The white area illustrates a dynamic range of the EEG amplifier (in this case 0V-3.3V) and the hatched area illustrates voltages falling outside of this dynamic range.

In comparison, FIG. 7B shows two complimentary sinusoids applied using the apparatus 200 shown in FIG. 2. The solid black line represents the signal delivered to the first stimulation electrode 204 and the dashed black line represents the complimentary signal applied to the second stimulation electrode. The dotted black line represents the common mode signal seen at the EEG amplifier. Driving the second stimulation electrode 206 with a voltage equal in magnitude and opposite in polarity to the voltage applied to the first stimulation electrode 204 causes summation of the two electrode voltages in the head, thus cancelling the head voltage with respect to a common reference. This causes the common mode signal seen at the EEG amplifier 208 (dotted line) to remain close to the zero voltage point.

Occasionally, however, it can be seen from FIG. 7B that the common mode signal falls below the lower limit of the linear range of the EEG amplifier input voltage (represented by the hatched area). FIG. 7C illustrates complimentary sinusoids applied using the apparatus 300 shown in FIG. 3. It can be seen that the addition of an additional summing circuit 317 that introduces an offset voltage (Voffset), shifts the common reference voltage seen by the tissue into the linear range of the EEG amplifier. The dotted black line represents the voltage of the bulk of the patient's head.

FIG. 7D shows two complimentary sinusoids applied using the apparatus 400 shown in FIG. 4. It can be seen that the addition of a higher gain differential at the second stimulation electrode 406 introduces an asymmetry into the voltage mirror to compensate for nonlinearities in the body. As explained above with reference to FIG. 4, a feedback signal is calculated as the common average of the voltage seen at the measurement electrodes 410, 412. This represents the common mode error signal which is coupled via the summing circuit 417 and inverting amplifier 420 to the second stimulation electrode 406, thus completing the negative feedback loop. The striped area illustrates the margin of voltage added to the second stimulation electrode 406 based on the feedback signal. By compensating for impedance imbalance at the electrodes 404, 406, 410, 412, the body ground reference (Vref) represented by the dotted black line is maintained at a constant level.

Embodiments described above have been implemented using transcranial electrodes attached to the surface of the head of a patient. The present disclosure is not, however, limited to the use of transcranial electrodes. In some embodiments, one or more of the electrodes described above may be replaced, for example, with intracranial electrodes placed on the surface of the brain and/or implanted within the brain (deep brain stimulation (DBS) and deep brain measurement (DBM)). Embodiments of the present invention may equally be implemented using capacitive electrodes for stimulation and/or measurement. The above described techniques for simultaneous electrical stimulation and measurement of neural activity are equally applicable to stimulation using the intracranial and/or capacitive electrodes described above.

Additionally, the techniques described above are not limited to improving stimulation and measurement of neural tissue in the brain. Embodiments described herein can be used for the stimulation and measurement of neural activity in any human or animal tissue. For example, embodiments may be used in the stimulation of digestive organs for gastrointestinal motility disorders. Embodiments may also be used in the functional stimulation (FES) of muscles, for example during rehabilitation. Embodiments of the present invention may also be used in electrocardiogram application where it may be advantageous to monitor the neural activity from muscle contractions in one part of a patient's heart whilst electrically stimulating muscles in another part of the patient's heart.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. An apparatus for performing bioelectric stimulation, the apparatus comprising:
 a stimulation unit;
 a measurement unit comprising an amplifier;
 first and second stimulation electrodes operable to apply electrical signals to tissue of a patient;
 first and second measurement electrodes operable to receive first and second measurement signals from the tissue of the patient;
 wherein the stimulation unit is configured to deliver a first stimulation signal to the first stimulation electrode and a second stimulation signal to the second stimulation electrode;
 wherein the first stimulation signal and the second stimulation signal are mirrored about a biasing voltage, the biasing voltage set in dependence of the dynamic range of the amplifier.

2. The apparatus of claim 1, wherein the measurement unit is configured to generate a signal in dependence of a voltage difference between the first measurement signal and the second measurement signal.

3. The apparatus of claim 2, wherein the measurement unit is configured to generate the signal in dependence of an average of the first measurement signal and the second measurement signal.

4. The apparatus of claim 1, wherein the first stimulation signal and the second stimulation signal are oscillating signals or pulsed signals or direct current (DC) signals.

5. The apparatus of claim 1, wherein the biasing voltage is set in dependence on the centre point of the dynamic range of the amplifier.

6. The apparatus of claim 1, wherein the stimulation unit and the measurement unit share a common reference voltage.

7. The apparatus of claim 6, wherein the biasing voltage is adjusted in dependence on a DC offset between the common reference voltage and a common mode voltage measured at the first and second measurement electrodes.

8. The apparatus of claim 7, wherein the biasing voltage is adjusted to reduce the DC offset between the common reference voltage and the common mode voltage measured at the first and second measurement electrodes.

9. The apparatus of claim 1, wherein the measurement unit comprises:
 a differential amplifier comprising:
  a first input coupled to the first measurement electrode,
  a second input coupled to the second measurement electrode, and
  an output.

10. The apparatus of claim 1, wherein the stimulation unit comprises:
 a current source having an output;
 an inverting amplifier having a non-inverting input and an inverting output; and
 a summing circuit having a first summing input, a second summing input and a summing output.

11. The apparatus of claim 10, wherein:
 the output of the current source is coupled to the first stimulation electrode and the first summing input;
 the inverting output of the inverting amplifier is coupled to the second stimulation electrode;
 the second summing input is coupled to a reference offset voltage; and
 the summing output is coupled to inverting input of the inverting amplifier.

12. The apparatus of claim 10, wherein the measurement unit includes a measurement circuit, wherein the measurement circuit comprises a feedback output and wherein the measurement circuit is configured to output, at the feedback output, a voltage proportional to an average of a voltage on the first measurement electrode and a voltage on the second measurement electrode.

13. The apparatus of claim 12, wherein:
 the output of the current source is coupled to the first stimulation electrode and the first summing input;
 the second summing input is coupled to the feedback output; and
 the inverting input is coupled to the summing output.

14. The apparatus of claim 13, further comprising a stimulation compensation filter coupled between the first output of the current source and the first summing input and/or a measurement compensation filter coupled between the feedback output and the second summing input.

15. The apparatus of claim 1, wherein the first and second measurement electrodes and/or the first and second stimulation electrodes are transcranial, transdermal or implanted in the brain.

16. A method of performing bioelectric stimulation, comprising:
 generating a first stimulation signal with a stimulation unit;
 generating a second stimulation signal with the stimulation unit, wherein the first stimulation signal and the second stimulation signal are mirrored about a biasing voltage, the biasing voltage set in dependence of a dynamic range of an amplifier;
 applying the first stimulation signal to a first stimulation electrode operable to couple electrical signals into tissue of a patient;
 applying the second stimulation signal to a second stimulation electrode operable to couple electrical signals into the tissue of the patient
 receiving first and second measurement signals from the tissue of the patient at first and second measurement electrodes; and
 amplifying the received electrical signals using a measurement unit comprising an amplifier.

17. The method of claim 16, further comprising: generating, with the measurement unit, a signal in dependence of a voltage difference between the first measurement signal and the second measurement signal.

18. The method of claim 17, wherein the measurement unit is configured to generate the signal in dependence of an average of the first measurement signal and the second measurement signal.

19. The method of claim 16, wherein the second stimulation signal and the signal are generated based on a common reference voltage.

20. The method of claim 19, further comprising: adjusting the biasing voltage in dependence on a DC offset between the common reference voltage and a common mode voltage of the first measurement signal and the second measurement signal.

* * * * *